United States Patent
Higashide

(10) Patent No.: US 11,679,057 B2
(45) Date of Patent: Jun. 20, 2023

(54) GOGGLE

(71) Applicant: SPORTS-NET Co., Ltd., Osaka (JP)

(72) Inventor: Kosuke Higashide, Osaka (JP)

(73) Assignee: SPORTS-NET Co., Ltd.

( * ) Notice: Subject to any disclaimer, the term of this patent is extended or adjusted under 35 U.S.C. 154(b) by 787 days.

(21) Appl. No.: 16/492,640

(22) PCT Filed: May 7, 2019

(86) PCT No.: PCT/JP2019/018285
§ 371 (c)(1),
(2) Date: Sep. 10, 2019

(87) PCT Pub. No.: WO2020/213176
PCT Pub. Date: Oct. 22, 2020

(65) Prior Publication Data
US 2021/0275384 A1    Sep. 9, 2021

(30) Foreign Application Priority Data

Apr. 18, 2019 (JP) .............................. JP2019-079679

(51) Int. Cl.
*A61H 5/00* (2006.01)
*A61F 9/02* (2006.01)
*G02C 7/16* (2006.01)

(52) U.S. Cl.
CPC ............... *A61H 5/00* (2013.01); *A61F 9/029* (2013.01); *G02C 7/16* (2013.01)

(58) Field of Classification Search
CPC .. A61F 9/02; A61F 9/028; A61F 9/026; A61F 9/022; A61F 2009/021;
(Continued)

(56) References Cited

U.S. PATENT DOCUMENTS 4,298,201 A    11/1981   Palinkas .................. 273/183 B
5,765,223 A *  6/1998   McCausland ...... A41D 13/1184
                                                       2/427
(Continued)

FOREIGN PATENT DOCUMENTS

CN         1912688 A      2/2007
CN       201223494 Y      4/2009
(Continued)

OTHER PUBLICATIONS

International Search Report dated Jun. 25, 2019 in corresponding PCT International Application No. PCT/JP2019/018285.
(Continued)

*Primary Examiner* — Nathan E Durham
*Assistant Examiner* — Abby M Spatz
(74) *Attorney, Agent, or Firm* — Ostrolenk Faber LLP

(57) ABSTRACT

A Goggle is provided which enables an improvement in skiing skills and techniques. A goggle 1 of the present invention comprises a lens body 11, a lens body supporting part 12 configured to support the lens body 11, a face plate part 13 positioned on a peripheral edge part behind the lens body supporting part 12, having flexibility and capable of coming into contact with a face of a wearer, and a gaze correcting part 14 provided in a center of the face plate part, having a rectangular column shape and enabling correction of a gaze of the wearer, the gaze correcting part 14 having mutually different colors on a facing surface 14a facing the wearer, a right side surface 14b located to the right of the facing surface 14a and a left side surface 14c located to the left of the facing surface 14a and dividing a field of view of the wearer into a right field of view and a left field of view.

9 Claims, 4 Drawing Sheets

(58) Field of Classification Search
CPC .. A61F 9/029; G02C 7/16; G02C 5/02; G02C 5/10; G02C 11/02; G02C 11/00; A61H 5/00
USPC .... 2/426, 431, 436, 445, 441, 439, 428, 440
See application file for complete search history.

(56) References Cited

U.S. PATENT DOCUMENTS

| | | | |
|---|---|---|---|
| 5,790,230 A * | 8/1998 | Sved | A61F 9/025 351/110 |
| 6,811,258 B1 * | 11/2004 | Grant | G02C 7/027 351/159.6 |
| 2003/0114256 A1 * | 6/2003 | Mathog | A63B 69/0053 473/422 |
| 2004/0025232 A1 | 2/2004 | Hartley et al. | 2/452 |
| 2005/0254001 A1 | 1/2005 | Winningham | 351/156 |
| 2006/0185066 A1 | 8/2006 | Page et al. | 2/424 |
| 2007/0226882 A1 * | 10/2007 | Ryan | A61F 9/025 2/426 |
| 2010/0186153 A1 | 7/2010 | Reyes | 2/427 |
| 2011/0131712 A1 * | 6/2011 | Sup | A63B 33/004 2/446 |
| 2013/0298318 A1 * | 11/2013 | Rogers | A61F 9/027 2/439 |
| 2017/0056742 A1 | 3/2017 | Glynn et al. | |
| 2018/0001182 A1 * | 1/2018 | Szanto | G02B 27/0176 |
| 2018/0052319 A1 | 2/2018 | Mccabe | |

FOREIGN PATENT DOCUMENTS

| | | |
|---|---|---|
| CN | 201558466 U | 8/2010 |
| CN | 101836916 A | 9/2010 |
| CN | 104423045 A | 3/2015 |
| CN | 105467613 A | 4/2016 |
| CN | 107242933 A | 10/2017 |
| CN | 108139599 A | 6/2018 |
| CN | 108474952 A | 8/2018 |
| JP | H5-245171 A | 9/1993 |
| JP | 3002411 U | 9/1994 |
| JP | 2012-515947 A | 7/2012 |
| KR | 10-2006-0013741 A | 2/2006 |
| KR | 10-2007-0014592 A | 2/2007 |

OTHER PUBLICATIONS

Written Opinion dated Jun. 25, 2019 in corresponding PCT International Application No. PCT/JP2019/018285.
Zhang et al., *Study on Effects of Target Color on Eye Pointing Tasks*, Computer Science, vol. 42, No. 9, Sep. 2015 (with English Abstract).

* cited by examiner

GOGGLE

CROSS-REFERENCE TO RELATED APPLICATIONS

The present application is a 35 U.S.C. §§ 371 national phase conversion of PCT/JP2019/018285, filed May 7, 2019, which claims priority to Japanese Patent Application No. 2019-079679, filed Apr. 18, 2019, the contents of both of which are incorporated herein by reference.

TECHNICAL FIELD

The present invention relates to a goggle, more particularly to a snow goggle capable of drastically improving skiing skills and skiing techniques.

BACKGROUND ART

In skiing and the like, a goggle plays a role in securing a field of view, protecting eyes and the like. Further, in the case of a goggle with a UV (ultraviolet) shielding function, protection from ultraviolet rays is also made. In recent years, various improvements such as weight saving, the provision of a defogging function and an improvement of a lens mounting technique have been added to make a goggle more comfortably wearable (for example, patent literature 1).

However, conventional goggles have not been used as exercise aids for more quick improvement of skiing performance.

PRIOR ART DOCUMENTS

Patent Documents

Patent Document 1: Japanese Unexamined Patent Application Publication (Translation of PCT Application) No. 2012-515947

SUMMARY OF INVENTION

Technical Problem

The present invention was developed in view of the above problem and aims to provide a goggle enabling an improvement in skiing skills and techniques.

Means for Solving the Problems

In order to solve the aforementioned problem, the goggle according to the present invention is a goggle comprises a lens body, a lens body supporting part configured to support the lens body, a face plate part positioned on a peripheral edge part behind the lens body supporting part, having flexibility and capable of coming into contact with a face of a wearer, and a gaze correcting part provided in a center of the face plate part, having a rectangular column shape and enabling correction of a gaze of the wearer, the gaze correcting part having mutually different colors on a facing surface facing the wearer, a right side surface located to the right of the facing surface and a left side surface located to the left of the facing surface and dividing a field of view of the wearer into a right field of view and a left field of view.

In the configuration described above, it is preferable that the gaze correcting part is attachably and detachably provided in a center of the face plate part.

In the configuration described above, it is preferable that the lens body is a left-and-right integrated lens body.

In the configuration described above, it is preferable that the gaze correcting part has elasticity.

Advantageous Effects of Invention

According to the present invention, the gaze correcting part enabling the correction of the gaze of the wearer is provided in the center of the face plate part positioned on the peripheral edge part behind the lens body supporting part supporting the lens body. This gaze correcting part has a rectangular column shape, and the right side surface located to the right of the facing surface facing the wearer and the left side surface located to the left of the facing surface have mutually different colors. Further, the facing surface has the color different from those of the right side surface and the left side surface.

Here, when a turn is made during downhill skiing, a gaze (eye line) is preferably stable (fixed) in a turning direction. In this way, a direction, an inclination and a front-rear position of a head can be controlled and a smooth turn can be made. If the gaze is not stable in the turning direction and the position of the head is unstable, problems into which many skiers fall such as rearward inclination, inward turnover and fatigue caused by repeated turns made while compensating for body unbalance by muscle strength occur when the turn is switched and smooth turns are difficult. However, the goggle of the present invention includes the gaze correcting part in the center of the face plate part and, in this gaze correcting part, the facing surface facing the wearer, the right side surface located to the right of the facing surface and the left side surface located to the left of the facing surface have three different colors. Thus, if the wearer makes a rightward turn, the color of the left side surface can be visually confirmed in the left field of view of the wearer. On the other hand, if the wearer makes a leftward turn, the color of the right side surface can be visually confirmed in the right field of view of the wearer. As just described, when a turn is made, the color of the right or left side surface of the gaze correcting part can be visually confirmed in the field of view on the side opposite to the turning direction, thereby correcting a behavior of the wearer to constantly make both left and right turns using his/her dominant eye. Further, when the turn is switched, the wearer can visually confirm the color of the facing surface. In this way, a rearward inclined posture of the wearer can be corrected by moving the position of the head in a forward inclining direction with respect to skis. As a result, the wearer can equally make left and right turns in a forward inclined posture and skiing skills, particularly skills in making turns can be drastically improved.

DESCRIPTION OF EMBODIMENT

A goggle according to an embodiment of the present invention is described below with reference to FIGS. 1 to 6.

Figure 1:
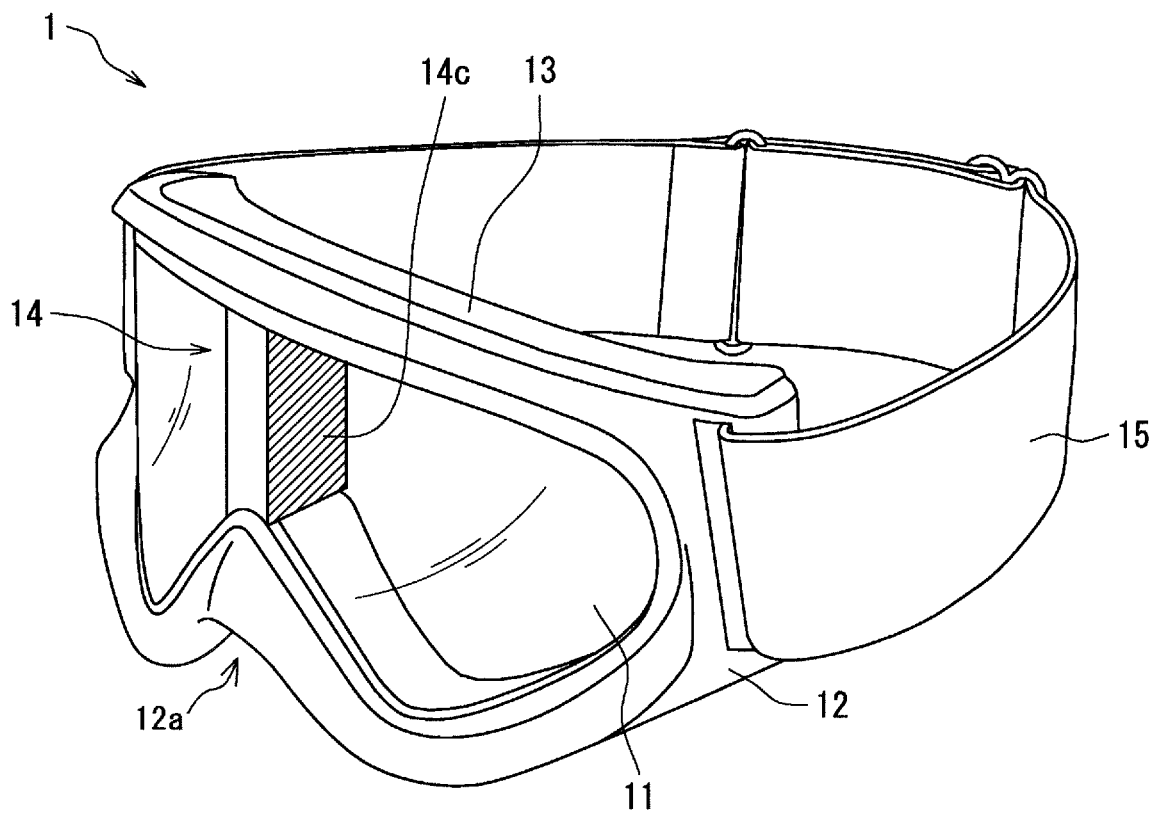
FIG. 1 is a perspective view schematically showing a goggle according to an embodiment of the present invention.
Figure 2:
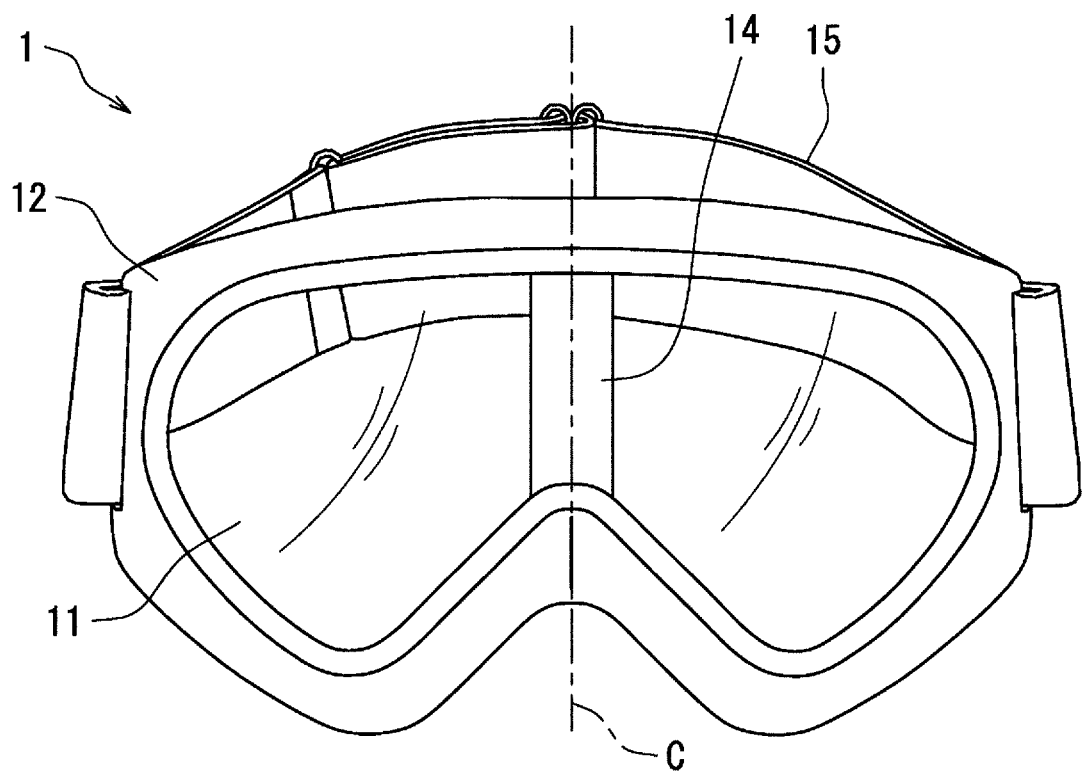
FIG. 2 is a front view schematically showing the goggle.
Figure 3:
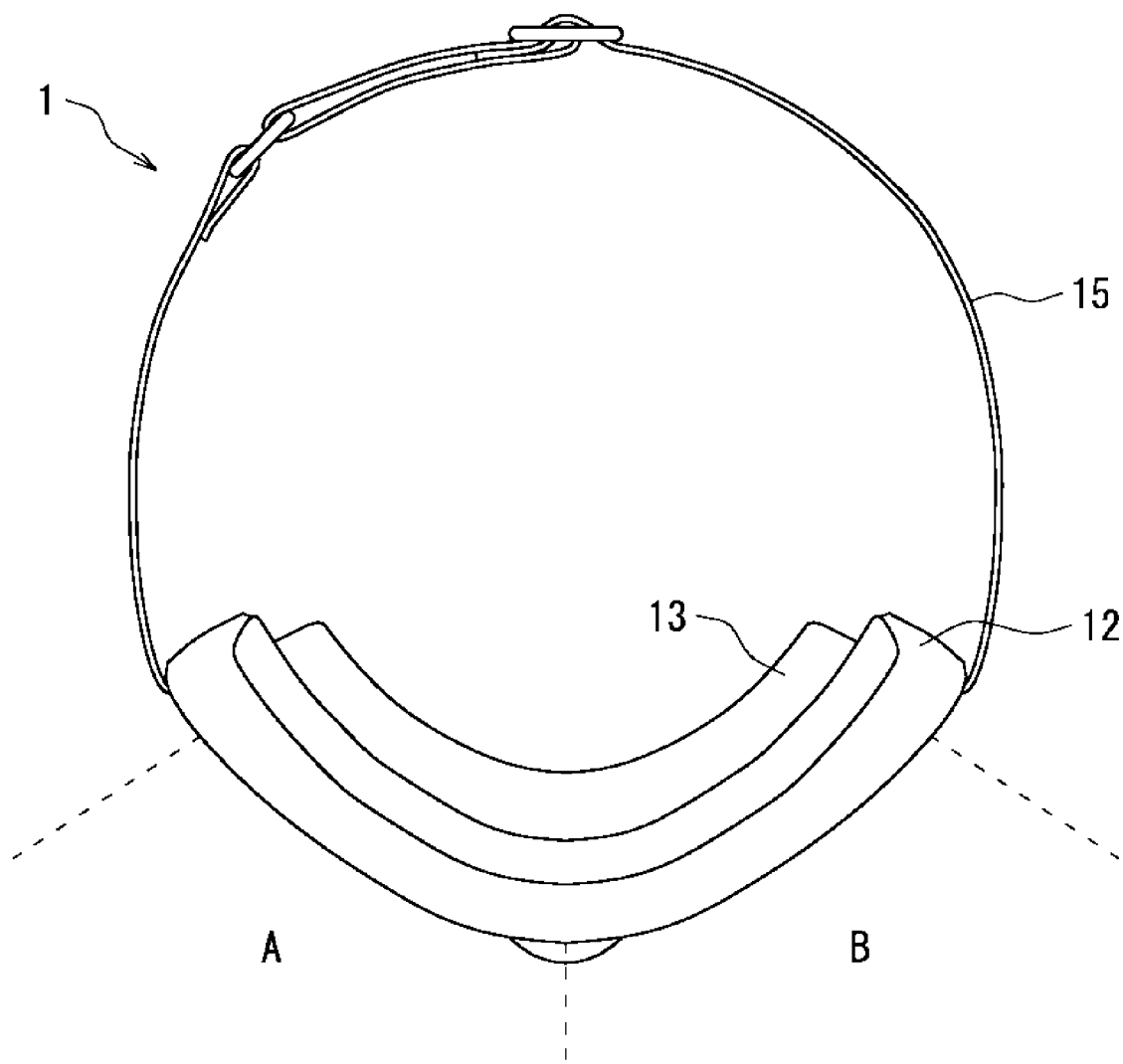
FIG. 3 is a plan view schematically showing the goggle.
Figure 4:
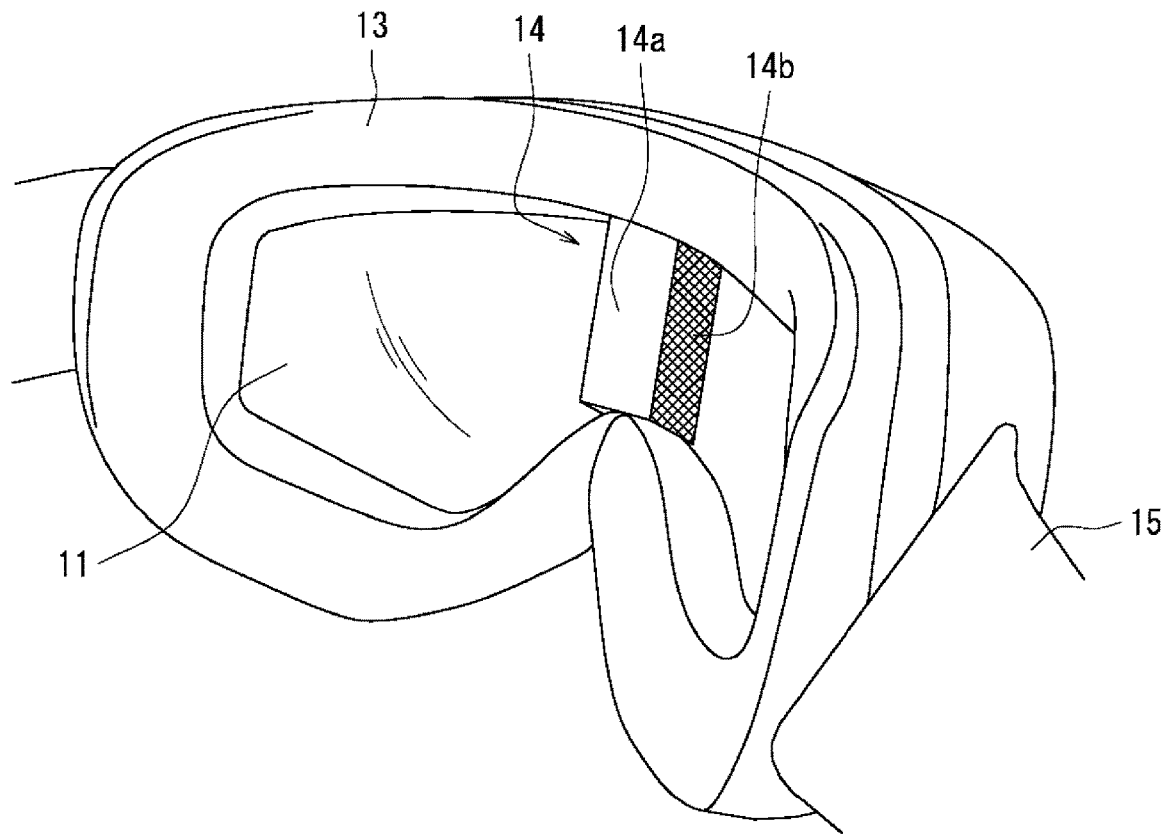
FIG. 4 is a perspective view of the goggle viewed from inside.
Figure 5:
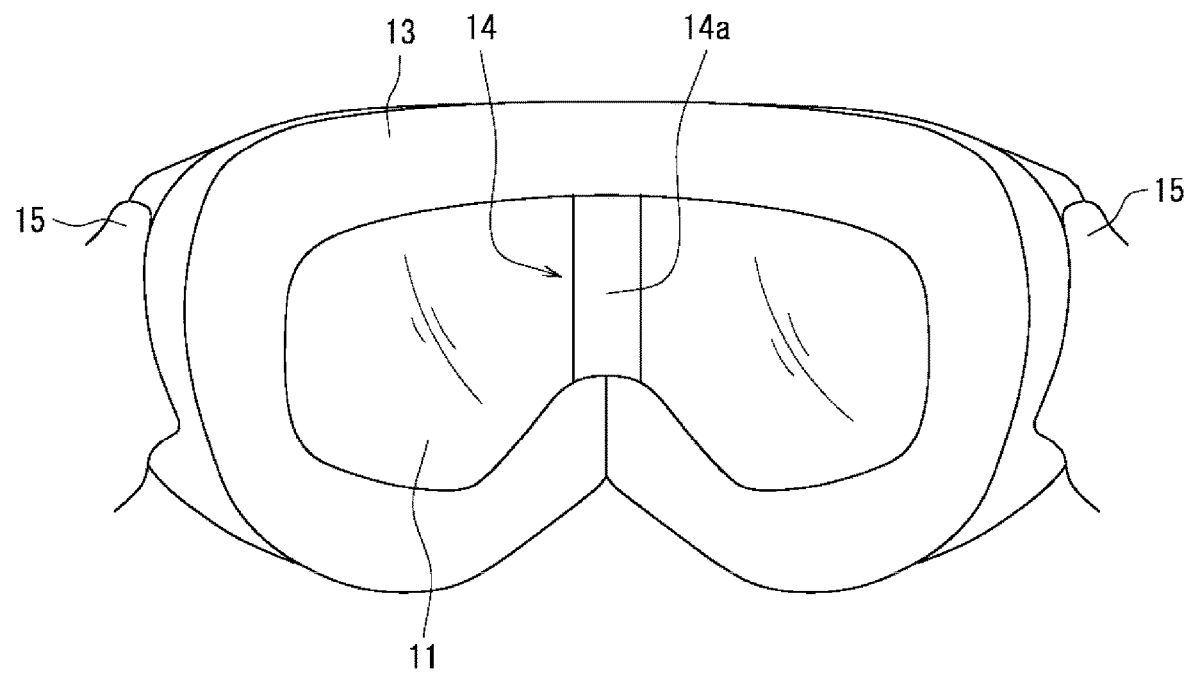
FIG. 5 is a back view schematically showing the goggle.
Figure 6:
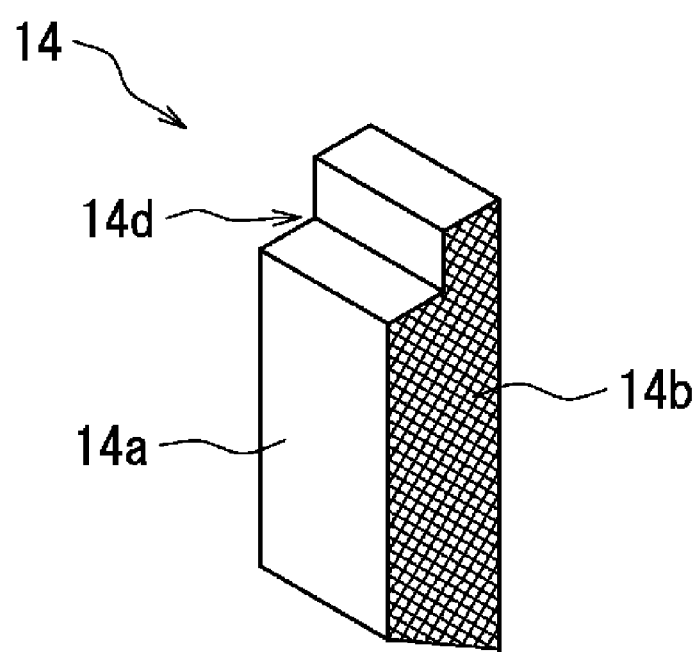
FIG. 6 is a perspective view schematically showing a gaze correcting part in the goggle.

Parts unnecessary for description are omitted and some parts are shown in an enlarged or reduced manner to facilitate description. FIG. 1 is a perspective view schematically showing the goggle according to the embodiment of the present invention. FIG. 2 is a front view schematically showing the goggle. FIG. 3 is a plan view schematically showing the goggle. FIG. 4 is a perspective view of the goggle viewed from inside. FIG. 5 is a back view schematically showing the goggle. FIG. 6 is a perspective view schematically showing a gaze correcting part in the goggle.

The goggle 1 according to the present embodiment includes at least a lens body 11, a lens body supporting part 12, a face plate part 13, a gaze correcting part 14 and a head holding part 15 as shown in FIGS. 1 to 3. The goggle 1 has a function of blocking particulate matters, water, snow and the like to protect the eyes of a wearer of the goggle 1 and peripheral regions thereof.

The lens body 11 is a left-and-right integrated lens body. The lens body 11 has a bilaterally symmetrically shape with a center line C shown in FIG. 1 as a line of symmetry. In this way, areas of a right field of view A and a left field of view B shown in FIG. 3 are made equal. It should be noted that the lens body 11 is not limited to the left-and-right integrated one, and may be separated lens bodies laterally separated with the center line C shown in FIG. 2 as a line of symmetry.

The lens body supporting part 12 is circumferentially closed and the outer shape thereof corresponds to that of the lens body 11. The lens body supporting part 12 is in contact with the periphery of the lens body 11. A recessed part 12a for positioning the goggle 1 on the nose bridge of the wearer is provided in a bottom part of the lens body supporting part 12. In this way, the goggle 1 of the present embodiment can expose the nose of the wearer to outside.

The face plate part 13 is positioned and provided on a peripheral edge part behind the lens body supporting part 12. The face plate part 13 is flexible, whereby the face plate part 13 can come into contact with the face of the wearer and the goggle 1 can fit to the surface of the face of the wearer. A material of the face plate part 13 is not particularly limited. For example, low-resilience sponge, rubber or the like can be used.

The gaze correcting part 14 has a rectangular parallelepiped overall shape and is provided in a center of the face plate part 13. Specifically, as shown in FIGS. 4 and 5, an upper part of the gaze correcting part 14 is fit into a clearance between the lens body 11 and the face plate part 13 and a lower part of the gaze correcting part 14 is locked to the recessed part 12a of the lens body supporting part 12, whereby the gaze correcting part 14 is provided in the center of the face plate part 13. In this way, the gaze correcting part 14 is attachable to and detachable from the goggle 1.

A step-like cut part 14d is provided on a corner part on the side of a facing surface 14a facing the wearer in the gaze correcting part 14. This cut part 14d presses and deforms the face plate part 13, thereby enabling the upper part of the gaze correcting part 14 to be fit into the clearance between the lens body 11 and the face plate part 13. It should be noted that although the step-like cut part 14d has been described as an example in the present embodiment, the present invention is not limited to this. The shape of the cut part 14d can be appropriately set according to the shapes of the lens body 11, the face plate part 13 and the like. Further, the gaze correcting part 14 may not include the cut part 14d.

Further, the bottom surface of the lower part of the gaze correcting part 14 is inclined toward the facing surface 14a to be described later to reduce an area of the facing surface 14a. The lower part of the gaze correcting part 14 can be locked to the recessed part 12a of the lens body supporting part 12 by the action of a restoring force of the face plate part 13 deformed by being pressed by the cut part 14d into an original shape. It should be noted that how much the bottom surface of the lower part of the gaze correcting part 14 is inclined is not particularly limited and can be appropriately set. Further, although the gaze correcting part 14 having the lower part with the inclined bottom surface has been described as an example in the present embodiment, the present invention is not limited to this and various shapes can be adopted.

Further, in the gaze correcting part 14, the facing surface 14a facing the wearer, a right side surface 14b located to the right of the facing surface 14a and a left side surface 14c located to the left of the facing surface have colors at least different from each other (see FIG. 6). In this way, a field of view of the wearer can be divided into the right field of view A and the left field of view B. When the wearer turns his/her gaze in a direction toward the left field of view, the right eye can visually confirm the color of the right side surface 14b. On the contrary, when the wearer turns his/her gaze in a direction toward the right field of view, the left eye can visually confirm the color of the left side surface 14c. Further, the facing surface 14a has the color different from those of the right side surface 14b and the left side surface 14c to enable clear visual confirmation of the colors of the right side surface 14b and the left side surface 14c. In this way, the wearer can visually confirm the color of the facing surface 14a every time a turn is switched.

It should be noted that the gaze correcting part 14 is not limited to the one having the rectangular parallelepiped shape and may have a rectangular column shape such as a polygonal column shape. Further, a combination of the colors of the facing surface 14a, the right side surface 14b and the left side surface 14c is not particularly limited. For example, it is preferable to employ a combination of colors largely different from each other such as the black facing surface 14a, the red right side surface 14b and the blue left side surface 14c.

A constituting material of the gaze correcting part 14 is not particularly limited, but a material having elasticity and excellent in processability is preferable. Examples of such a constituting material include low-resilience sponge and rubber.

The head holding part 15 enables the goggle 1 to be fixed to a head part of the wearer when the goggle 1 is used. Specifically, the wearer positions the face plate part 13 on his/her face surface and adjusts the head holding part 15 surrounding a rear side of the head part, whereby the face plate part 13 is firmly, but comfortably fixed in position.

REFERENCE SIGNS LIST 1 goggle
11 lens body
12 lens body supporting part
12a recessed part
13 face plate part
14 gaze correcting part
14a facing surface
14b right side surface
14c left side surface
14d cut part
15 head holding part

The invention claimed is:
1. A goggle, comprising:
a lens body;

a lens body supporting part configured to support the lens body;
a face plate part positioned on a peripheral edge part behind the lens body supporting part, having flexibility and capable of coming into contact with a face of a wearer; and
a gaze correcting part provided in a center of the face plate part, formed with a polygonal column and enabling correction of a gaze of the wearer; wherein
the gaze correcting part has, in the polygonal column, mutually different colors on a facing surface configured to face the wearer, a right side surface located to the right of the facing surface and a left side surface located to the left of the facing surface and divides a field of view of the wearer into a right field of view and a left field of view; and
the gaze correcting part includes a step cut part on a corner part on a side of the facing surface configured to face the wearer.

2. The goggle according to claim 1, wherein the gaze correcting part is attachably and detachably provided in a center of the face plate part.

3. The goggle according to claim 1, wherein the lens body is a left-and-right integrated lens body.

4. The goggle according to claim 1, wherein the gaze correcting part has elasticity.

5. The goggle according to claim 1, wherein a bottom surface of a lower part of the gaze correcting part is inclined toward the facing surface to reduce an area of the facing surface.

6. A goggle, comprising:
a lens body;
a lens body supporting part configured to support the lens body;
a face plate part positioned on a peripheral edge part behind the lens body supporting part, having flexibility and capable of coming into contact with a face of a wearer; and
a gaze correcting part provided in a center of the face plate part, formed with a polygonal column and enabling correction of a gaze of the wearer; wherein
the gaze correcting part has, in the polygonal column, mutually different colors on a facing surface configured to face the wearer, a right side surface located to the right of the facing surface and a left side surface located to the left of the facing surface and divides a field of view of the wearer into a right field of view and a left field of view, and
a bottom surface of a lower part of the gaze correcting part is inclined toward the facing surface to reduce an area of the facing surface.

7. The goggle according to claim 6, wherein the gaze correcting part is attachably and detachably provided in a center of the face plate part.

8. The goggle according to claim 6, wherein the lens body is a left-and-right integrated lens body.

9. The goggle according to claim 6, wherein the gaze correcting part has elasticity.

* * * * *